(12) United States Patent
Sanders

(10) Patent No.: US 7,789,897 B2
(45) Date of Patent: Sep. 7, 2010

(54) PEDICLE SCREW SPINAL ROD CONNECTOR ARRANGEMENT

(75) Inventor: Elliot H. Sanders, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 923 days.

(21) Appl. No.: 11/402,014

(22) Filed: Apr. 11, 2006

(65) Prior Publication Data

US 2007/0270810 A1    Nov. 22, 2007

(51) Int. Cl.
   *A61B 17/70*     (2006.01)
(52) U.S. Cl. ..................................... 606/278
(58) Field of Classification Search ................. 606/250, 606/277, 278, 268
   See application file for complete search history.

(56) References Cited

U.S. PATENT DOCUMENTS

| | | | |
|---|---|---|---|
| 5,304,177 A | | 4/1994 | Pennig |
| 5,330,473 A | * | 7/1994 | Howland ..................... 606/250 |
| 5,507,746 A | | 4/1996 | Lin |
| 5,584,831 A | * | 12/1996 | McKay ...................... 606/86 A |
| 5,676,665 A | | 10/1997 | Bryan |
| 5,947,966 A | | 9/1999 | Drewry et al. |
| 5,989,250 A | | 11/1999 | Wagner et al. |
| 6,113,600 A | | 9/2000 | Drummond et al. |
| 6,136,002 A | * | 10/2000 | Shih et al. .................... 606/250 |
| 6,136,003 A | | 10/2000 | Hoeck et al. |
| 6,248,104 B1 | | 6/2001 | Chopin et al. |
| 6,402,751 B1 | | 6/2002 | Hoeck et al. |
| 6,413,258 B1 | | 7/2002 | Bernhardt, Jr. |
| 6,520,962 B1 | | 2/2003 | Taylor et al. |
| 6,866,664 B2 | | 3/2005 | Schär |
| 2003/0045878 A1 | | 3/2003 | Petit et al. |
| 2003/0171751 A1 | | 9/2003 | Ritland |
| 2003/0176862 A1 | | 9/2003 | Taylor et al. |
| 2004/0039388 A1 | | 2/2004 | Biedermann et al. |
| 2005/0096654 A1 | | 5/2005 | Lin |
| 2005/0131404 A1 | * | 6/2005 | Mazda et al. ................. 606/61 |
| 2005/0143737 A1 | * | 6/2005 | Pafford et al. ................ 606/61 |
| 2005/0228382 A1 | * | 10/2005 | Richelsoph et al. .......... 606/61 |
| 2005/0240180 A1 | * | 10/2005 | Vienney et al. .............. 606/61 |
| 2006/0025770 A1 | | 2/2006 | Schalapfer et al. |
| 2006/0058787 A1 | | 3/2006 | David |

* cited by examiner

*Primary Examiner*—Eduardo C Robert
*Assistant Examiner*—Elana B Fisher

(57) ABSTRACT

A pedicle screw spinal rod connector arrangement is provided that includes in a body having an opening for mounting a head of an inserted pedicle screw. A bracket connected with the body forms a lateral restraint. A bridge is connected with and extends over the body. A spinal rod-receiving slot is provided between the bridge and the bracket. The connector arrangement also has a wedge axially offset from the pedicle screw moveable downward by a setscrew mounted with the bridge. The wedge imparts a locking force on the pedicle screw head and a generally lateral locking force on the spinal rod.

19 Claims, 3 Drawing Sheets

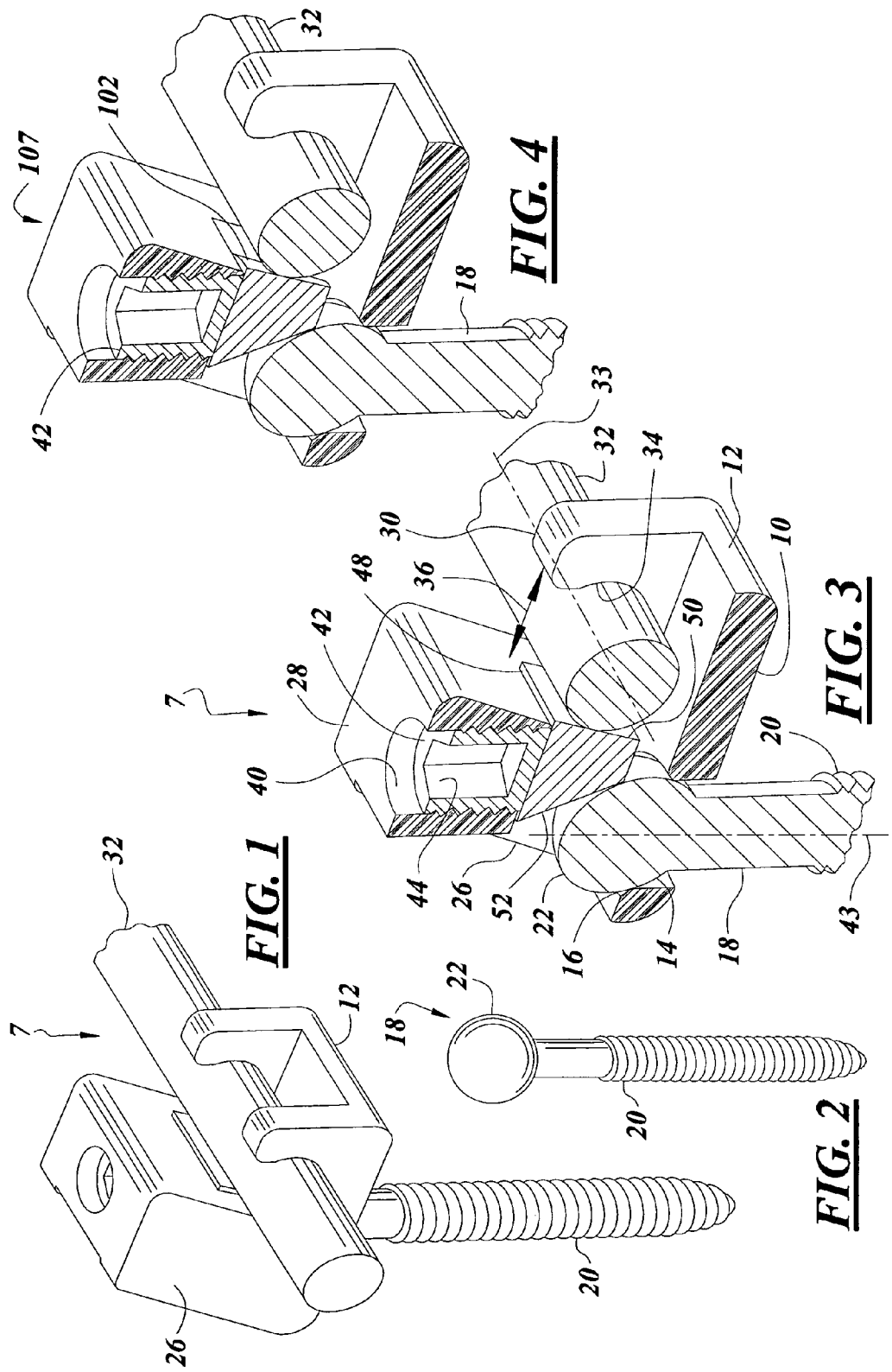

PEDICLE SCREW SPINAL ROD CONNECTOR ARRANGEMENT

FIELD OF THE INVENTION

The present invention relates to pedicle screw spinal rod connectors.

BACKGROUND OF THE INVENTION

Spinal surgeons often treat spinal disorders with spinal fusion augmented with elongated spinal rods connected to the spine with pedicle screws. Such "rod assemblies" generally comprise one or two spinal rods and a plurality of screws inserted through the pedicles and into their respective vertebral bodies. The screws are provided with connectors, for coupling the spinal rods to the screws. The spinal rods extend along the longitudinal axis of the spine, coupling to the plurality of screws via their connectors. The aligning influence of the rods forces the patient's spine to conform to a more appropriate shape.

SUMMARY OF THE INVENTION

The present invention provides a pedicle screw spinal rod connector arrangement that in a preferred embodiment includes a body having an opening for mounting a head of an inserted pedicle screw. A bracket connected with the body forms a lateral restraint. A bridge is connected with and extends over the body. A spinal rod-receiving slot is provided between the bridge and the bracket. The connector arrangement also has a wedge axially offset from the pedicle screw moveable downward by a setscrew mounted with the bridge. The wedge imparts a locking force on the pedicle screw head and a generally lateral locking force on the spinal rod.

Other features of the invention will become more apparent to those skilled in the art as the invention is further revealed in the accompanying drawings and Detailed Description of the Invention.

BRIEF DESCRIPTION OF THE DRAWINGS

FIG. 1 is a perspective view of a preferred embodiment pedicle screw spinal rod connector arrangement according to the present invention.

FIG. 2 it is a perspective view the pedicle screw utilized in the connector arrangement shown in FIG. 1.

FIG. 3 is a perspective view partially sectioned of the connector arrangement shown in FIG. 1.

FIG. 4 is a view similar to FIG. 3 of an alternative preferred embodiment connector arrangement.

DETAILED DESCRIPTION OF THE INVENTION

Figure 3A:
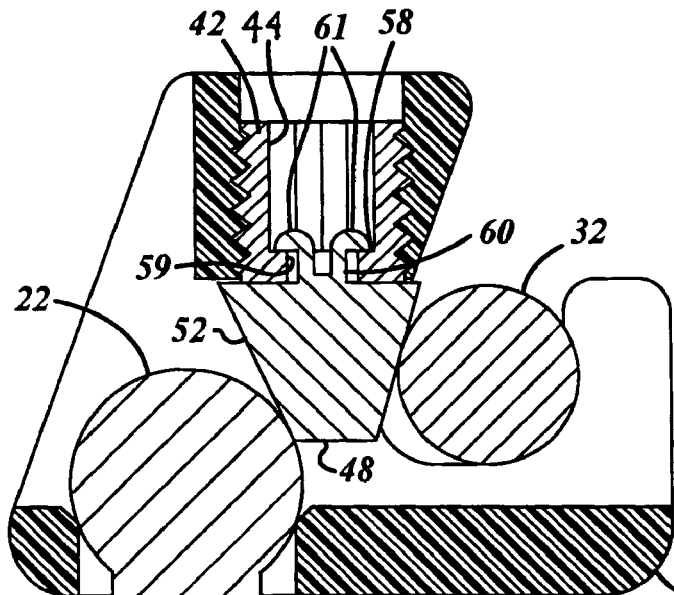
FIG. 3A is an enlarged sectional view of the connector arrangement shown in FIG. 3 illustrating additional detail of a connection of a setscrew and wedge shown in FIG. 3.

Referring to FIGS. 1-3 and 3A, a preferred embodiment pedicle screw spinal rod connector arrangement 7 according to the present invention is provided. The arrangement 7 includes a body 10. The body 10 is typically fabricated from a titanium or other suitable material. A bottom portion 12 of the body is planar with machined edges. The bottom portion 12 of the body has an opening 14. The opening 14 has a tapered edge 16. The opening 14 allows for the insertion of a pedicle screw 18.

The pedicle screw 18 is typically inserted into a pedicle of a patient's spinal column. The pedicle screw 18 has a mostly threaded shaft 20 that is connected with a conic, spherical, or semi-spherical head 22.

Two parallel spaced side plates 26 are fixedly connected with the bottom portion 12 of the body. Typically, the side plates 26 and bottom portion 12 are machined from a solid piece of material or are molded. Integrally connected with the side plates 26 and extending over the same is a bridge 28. A front portion of the side plates 26 forms dual brackets 30. The brackets 30 typically have a curved mating surface 34 that conforms to the cylindrical surface of a spinal rod 32 with single point or continuous contact with the spinal rod 32. A spacing between the bridge 28 and the brackets 30 forms a spinal rod-receiving slot 36.

The bridge 28 has a bore 40 that is at least partially threaded. Threadably inserted in the bore 40 is a setscrew 42. The setscrew 42 has along its top surface a depression forming a hex head torsion drive surface 44 for receipt of an Allen wrench (not shown). Positioned underneath the setscrew 42 is a wedge 48. The wedge 48 is positioned to be axially offset from an axis 43 of the pedicle screw 18. As shown in FIG. 3, the wedge 48 has a trapezoidal shape in cross-section with a generally flat spinal rod contact surface 50 and an opposed generally flat screw head contact surface 52. The wedge 48 is fabricated from a metallic generally hard material such as titanium or other suitable material.

The setscrew torsion drive surface 44 has a floor 58. An aperture 59 intersects the floor 58. Connected with the wedge 48 is a post 60 that extends through the aperture 59 and into the torsion drive surface 44. The width of the posts 60 is significantly smaller than that of the aperture 59 to facilitate lateral movement of the wedge 48 with the setscrew 42 and to allow the setscrew 42 to rotate freely with respect to the wedge 48. An end 61 of the post is deformed by swaging to enlarge the end 61 with respect to the aperture 59. The enlargement of the post end 61 captures the wedge 48 with the setscrew 42. The end 61 typically will have at least a slight clearance with the floor 58 to ensure that the wedge 48 can have the aforementioned relative movement with respect to the setscrew 42.

In operation the body 10, setscrew 42, and wedge 48 are assembled before delivery to an operating room. During a surgical operation, a surgeon inserts the head pedicle screw 18 into the opening 14 of the body 10. The shank 20 of the pedicle screw 18 is then threadably inserted within a vertebrate pedestal of the patient's spinal column. The spinal rod 32 is them placed within the spinal rod receiving slot 36 and is abutted by the brackets 30. The wedge 48 juxtaposes the spinal rod 32 and the screw head 22. The setscrew 42 is torqued causing the wedge 48 to be moved downward. The downward movement of the wedge 48 causes line contact along the context surface 50 of the wedge 48 with the spinal rod 32. The above noted action causes the brackets 30 to act as lateral restraints on the spinal rod 32. According the wedge 48 and brackets 30 combine to laterally lock the spinal rod 32. Simultaneously the downward movement of the wedge 48 causes the contact surface 52 of the wedge 48 to impart a locking force with a substantial downward component on the screw head 22 against the tapered edge 16 of the opening 14. Non-perpendicular alignment of the pedicle screw axis 43 with the bottom portion 12 of the body can be compensated for by the pivotal movement of the screw head 22 with the opening tapered edge 16. Lateral misalignment of a position of axis 43 with a centerline 33 of the spinal rod 32 can also be compensated by a depth of penetration of the setscrew 42 required to cause the wedge 48 to lock the pedicle screw 18 and the spinal rod 32. The wedge 48 can also move laterally slightly with respect to the setscrew 42 to compensate for tolerance differences. The line contact between the contact surface 50 of the wedge 48 and the spinal rod 32 insurers that the wedge 48 is non-rotative.

Typically, in most applications the context surface 50 line contact with spinal rod 32 is parallel with the axial centerline 33 of the spinal rod. The contact surface 50 line contact with the rod 32 is also parallel with a line drawn between the two brackets 30 and their point or line contact with the spinal rod 32. For applications for tapered spinal rods, the configuration of the brackets 30 contact points or lines and the line of contact of the contact surface 50 can be modified to be non-parallel to accommodate such tapered spinal rods. In addition, the contact surface 50 can be modified to provide single or multiple contact with a spinal rod 32 if so desired.

FIG. 4 presents an alternate preferred embodiment pedicle screws spinal rod connector arrangement 107 of the present invention. The components of FIG. 4 are essentially identical to those previously described in FIGS. 1-3 except that the wedge 102 is shaped as a symmetrical cone. During the tourqing of the setscrew 42, the wedge 102 can rotate slightly. Additionally the spinal rod 32 can have point contact with the wedge 102. In another embodiment, not shown, a cone shaped wedge can be integrally formed with the setscrew.

Figure 5:
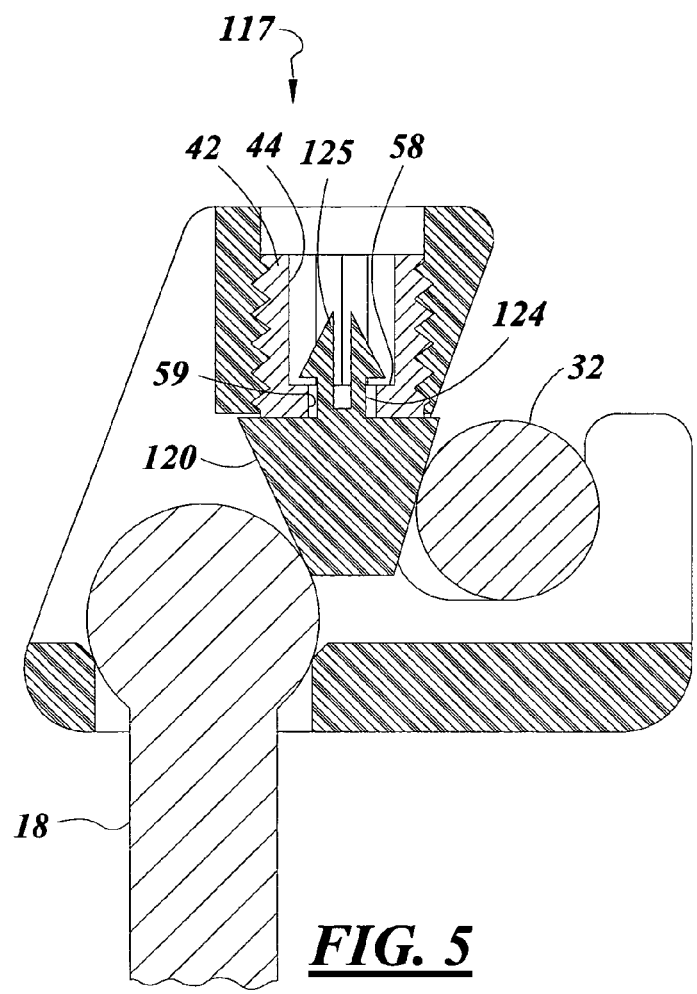
FIG. 5 is a view similar to FIG. 3A of another alternative preferred embodiment connector arrangement.

FIG. 5 presents an alternate preferred embodiment pedicle screw spinal rod connector arrangement 117 of the present invention. In the connector arrangement 117, the wedge 120 is fabricated from a polymeric material that is generally soft and deformable as compared with a metallic wedge. The wedge 120 has a post 124 with a deformable end 125. The insertion of the post 124 into the aperture 59 caused the end 125 radially contract and then extend outward to connect the wedge 120 with the setscrew 42.

Figure 6:
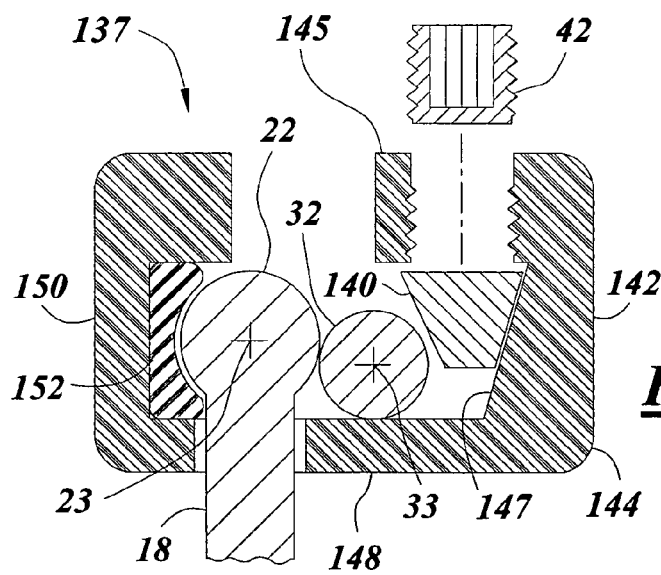

FIG. 6 presents an alternate preferred embodiment pedicle screws spinal rod connector arrangement 137 of the present invention. In the connector arrangement 137, the wedge 140 is positioned adjacent an extreme end 142 of the body 144. The wedge 140 is also adjacent the spinal rod 32. The connector arrangement 137 also has a bridge 145 that mounts a setscrew 42. Downward movement of the setscrew 42 causes the wedge 140 to aligned along an inclined alignment wall 147. The alignment wall 147 is connected with the bridge 145 and a lower body portion 148. A bracket 150 is also provided adjacent the pedicle screw head 22. Adjacent the bracket 150 is polymeric pedicle screw bumper 152. Downward movement of the wedge 140 imparts a lateral locking force on the spinal rod 32. The spinal rod 32 imparts a lateral locking force on the screw head 22 locking the screw head 22 against the bracket 150 via though the bumper 152. Typically, the locking force on the screw head 22 will additionally have a vertically upward component due to the fact that the rod axial centerline 33 is under a radius center 23 of the screw head.

Figure 7:
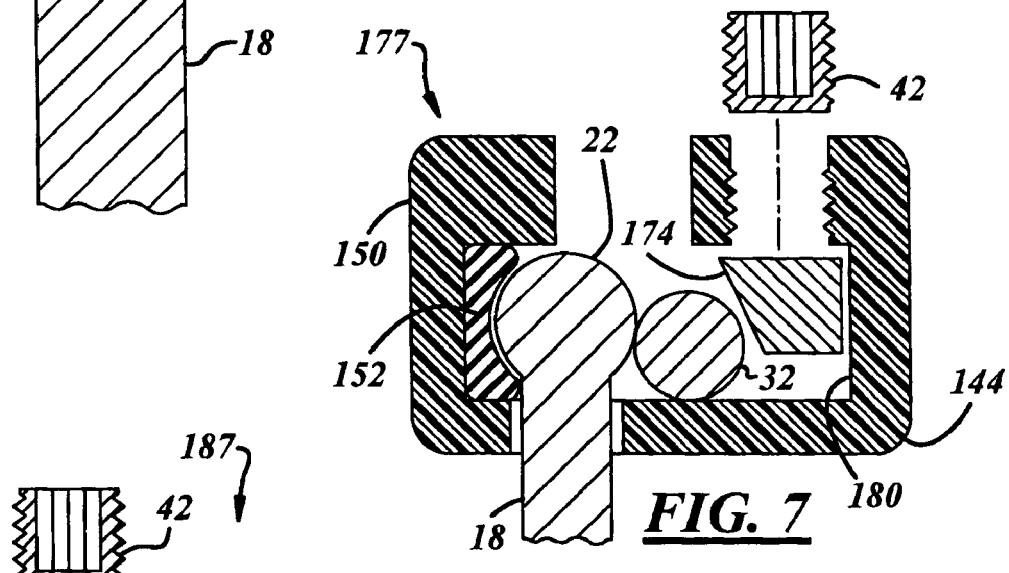
FIGS. 6, 7 and 8 are sectional views of additional alternate preferred embodiment connector arrangements to that shown in FIG. 1.

FIG. 7 presents an alternate preferred embodiment pedicle screws spinal rod connector arrangement 177 of the present invention. The arrangement 177 is essentially identical to that shown in FIG. 6 except that the alignment wall 180 is vertical and not inclined. Additionally the wedge 174 is somewhat modified.

Figure 8:
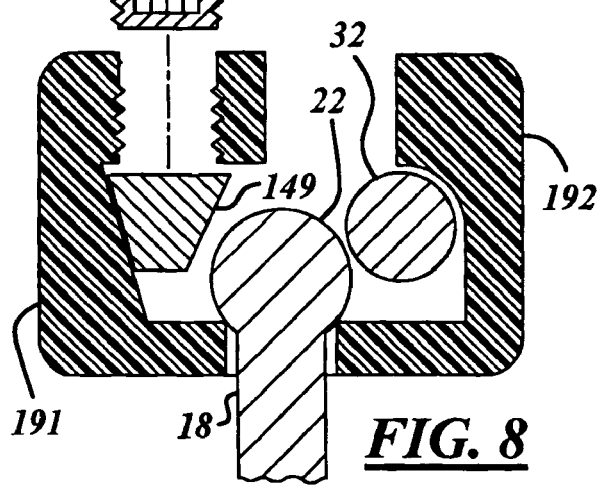

FIG. 8 presents an alternate preferred embodiment pedicle screws spinal rod connector arrangement 187 of the present invention. The arrangement 187 is essentially identical to that shown in FIG. 6 except that the positions of the spinal rod 32 and screw head 22 have been exchanged causing the wedge 149 to be adjacent the screw head 22. The wedge 149 is also adjacent and an extreme end 191 of the body. A bracket 192 laterally restrains the spinal rod 32.

While preferred embodiments of the present invention have been disclosed, it is to be understood it has been described by way of example only, and various modifications can be made without departing from the spirit and scope of the invention as it is encompassed in the following claims.

The invention claimed is:

1. A pedicle screw spinal rod connector arrangement comprising:
   a body having a bottom wall portion defining an opening with a head of an inserted pedicle screw mounted adjacent said opening;
   a bracket connected with said body forming a lateral restraint;
   a bridge extending over and connected with said body, said bridge defining an at least partially threaded bore, said bridge forming a spinal rod receiving slot between itself and said bracket with a spinal rod received within said slot; and
   a non-rotative wedge axially offset from said pedicle screw moveable downward by a setscrew threadably mounted within said bore in said bridge wherein said setscrew is rotatable relative to said wedge with said wedge positioned underneath said bore in said bridge and beneath a portion of said setscrew threadably engaged within said bore and with a lower portion of said setscrew engaging said wedge to move said wedge downward, said wedge imparting a locking force having a downward component on said head of said pedicle screw with said head engaged in contact against said bottom wall portion of said body adjacent said opening, said wedge imparting a generally lateral locking force on said spinal rod.

2. A pedicle screw spinal rod connector arrangement as described in claim 1 wherein said wedge is positioned laterally between said spinal rod and said head of said pedicle screw with said wedge positioned in contact with both said spinal rod and said head of said pedicle screw.

3. A pedicle screw spinal rod connector arrangement as described in claim 1 wherein said wedge is generally adjacent an extreme end of said body; and
   wherein said wedge is aligned by engagement of an outer surface of said wedge with an alignment wall defined by said extreme end of said body.

4. A pedicle screw spinal rod connector arrangement as described in claim 1 wherein said wedge is formed from a polymeric material.

5. A pedicle screw spinal rod connector arrangement as described in claim 1 wherein said setscrew freely rotates relative to said wedge.

6. A pedicle screw spinal rod connector arrangement as described in claim 1 wherein said spinal rod receiving slot formed between said bridge and said bracket includes an upwardly facing opening to allow top loading of said spinal rod into said spinal rod receiving slot.

7. A pedicle screw spinal rod connector arrangement comprising:
   a body having a bottom wall portion defining an opening with a head of an inserted pedicle screw mounted adjacent said opening;
   a bracket connected with said body forming a lateral restraint;
   a bridge extending over and connected with said body, said bridge defining an at least partially threaded bore, said bridge forming a spinal rod receiving slot between itself and said bracket with a spinal rod received within said slot; and a non-rotative wedge axially offset from said pedicle screw moveable downward by a setscrew threadably mounted within said bore in said bridge wherein said setscrew is rotatable relative to said wedge with said wedge positioned underneath said setscrew and with a lower portion of said setscrew engaging said wedge to move said wedge downward, said wedge imparting a locking force having a downward component on said head of said pedicle screw with said head engaged in contact against said bottom wall portion of said body adjacent said opening, said wedge imparting a generally lateral locking force on said spinal rod; and wherein said wedge is connected with a post, said post extending through an aperture in said setscrew, said post having an enlarged end with respect to said aperture.

8. A pedicle screw spinal rod connector arrangement comprising:
a body having a bottom wall portion defining an opening with a head of an inserted pedicle screw mounted adjacent said opening;
a bracket connected with said body forming a lateral restraint;
a bridge extending over and connected with said body, said bridge forming a spinal rod receiving slot between itself and said bracket with a spinal rod received within said slot; and
a non-rotative wedge axially offset from said pedicle screw moveable downward by a setscrew mounted with said bridge wherein said setscrew is rotatable relative to said wedge, wherein said wedge is laterally movably with respect to said setscrew when said setscrew is threadably engaged within an at least partially threaded bore in said bridge, said wedge imparting a locking force having a downward component on said head of said pedicle screw with said head engaged in contact against said bottom wall portion of said body adjacent said opening, said wedge imparting a generally lateral locking force on said spinal rod.

9. A pedicle screw spinal rod connector arrangement as described in claim 8 wherein said wedge is positioned underneath said bore in said bridge and beneath a portion of said setscrew threadably engaged within said bore.

10. A pedicle screw spinal rod connector arrangement comprising:
a body with a generally planer portion having an opening for mounting a generally spherical head of an inserted pedicle screw;
a bracket connected with said body forming a lateral restraint;
a bridge extending over and connected with said body, said bridge defining an at least partially threaded bore, said bridge forming a spinal rod receiving slot between itself and said bracket; and
a non-rotative wedge juxtaposing said pedicle screw and a rod received in said spinal rod receiving slot, said wedge being moveable downward by a set screw threadably mounted within said bore in said bridge wherein said set screw is rotatable relative to said wedge with said wedge positioned underneath said bore in said bridge and beneath a portion of said set screw threadably engaged within said bore and with a lower portion of said set screw engaging said wedge to move said wedge downward, said wedge imparting a downward locking force on said pedicle screw head and a lateral locking force on a spinal rod against said bracket.

11. A pedicle screw spinal rod connector arrangement as described in claim 10 wherein said wedge has a flat contact surface with line contact with said spinal rod.

12. A pedicle screw spinal rod connector arrangement as described in claim 11 wherein said line contact of said wedge with said spinal rod is parallel with a line joining points of contact of said bracket with said spinal rod.

13. A pedicle screw spinal rod connector arrangement as described in claim 11 wherein said line contact of said wedge with said spinal rod is non-parallel with a line joining points of contact of said bracket with said spinal rod.

14. A pedicle screw spinal rod connector arrangement as described in claim 10 wherein said bracket comprises dual parallel spaced brackets formed from sidewalls connected with said generally planar portion of said body, said dual parallel spaced brackets providing said lateral restraint.

15. A pedicle screw spinal rod connector arrangement as described in claim 10 wherein said spinal rod receiving slot formed between said bridge and said bracket includes an upwardly facing opening to allow top loading of said spinal rod into said spinal rod receiving slot.

16. A pedicle screw spinal rod connector arrangement comprising:
a body having a bottom wall portion defining an opening with a head of an inserted pedicle screw mounted adjacent said opening;
a bracket connected with said body forming a lateral restraint;
a bridge extending over and connected with said body, said bridge defining an at least partially threaded bore, said bridge forming a spinal rod receiving slot between itself and said bracket with a spinal rod received within said slot; and
a non-rotative wedge axially offset from said pedicle screw moveable downward by a setscrew threadably mounted within said bore in said bridge wherein said setscrew is rotatable relative to said wedge with said wedge positioned underneath said setscrew and with a lower portion of said setscrew engaging said wedge to move said wedge downward, said wedge imparting a locking force having a downward component on said head of said pedicle screw with said head engaged in contact against said bottom wall portion of said body adjacent said opening, said wedge imparting a generally lateral locking force on said spinal rod; and
wherein said wedge has a first tapered outer contact surface and a second tapered outer contact surface opposite said first tapered outer contact surface, said wedge positioned laterally between said head of said pedicle screw and said spinal rod with said first tapered outer contact surface engaged in contact with said spinal rod and said second tapered outer contact surface engaged in contact with said head of said pedicle screw.

17. A pedicle screw spinal rod connector arrangement comprising:
a body with a generally planer portion having an opening for mounting a generally spherical head of an inserted pedicle screw;
a bracket connected with said body forming a lateral restraint;
a bridge extending over and connected with said body, said bridge defining an at least partially threaded bore, said bridge forming a spinal rod receiving slot between itself and said bracket; and a non-rotative wedge juxtaposing said pedicle screw and a rod received in said spinal rod receiving slot, said wedge being moveable downward by a set screw threadably mounted with in said bore in said bridge wherein said set screw is rotatable relative to said wedge with said wedge positioned underneath said set screw and with a lower portion of said set screw engaging said wedge to move said wedge downward, said wedge imparting a downward locking force on said pedicle screw head and a lateral locking force on a spinal rod against said bracket; and wherein said wedge has a first tapered outer contact surface and a second tapered outer contact surface opposite said first tapered outer contact surface, said wedge positioned laterally between said generally spherical head of said pedicle screw and said spinal rod with said first tapered outer contact surface engaged in contact with said spinal rod and said second tapered outer contact surface engaged in contact with said generally spherical head of said pedicle screw.

18. A pedicle screw spinal rod connector arrangement comprising:

a body having a bottom wall portion defining an opening with a head of an inserted pedicle screw mounted adjacent said opening;

a bracket connected with said body forming a lateral restraint;

a bridge extending over and connected with said body, said bridge defining an at least partially threaded bore, said bridge forming a spinal rod receiving slot between itself and said bracket with a spinal rod received within said slot; and a non-rotative wedge axially offset from said pedicle screw moveable downward by a setscrew threadably mounted within said bore in said bridge wherein said setscrew is rotatable relative to said wedge with said wedge positioned underneath said setscrew and with a lower portion of said setscrew engaging said wedge to move said wedge downward, said wedge imparting a locking force having a downward component on said head of said pedicle screw with said head engaged in contact against said bottom wall portion of said body adjacent said opening, said wedge imparting a generally lateral locking force on said spinal rod; and wherein said wedge is trapezoidal shaped in cross section and includes a first outer contact surface and a second outer contact surface opposite said first outer contact surface, said wedge positioned laterally between said head of said pedicle screw and said spinal rod with said first outer contact surface engaged in contact with said spinal rod and said second outer contact surface engaged in contact with said head of said pedicle screw.

19. A pedicle screw spinal rod connector arrangement comprising:

a body with a generally planer portion having an opening for mounting a generally spherical head of an inserted pedicle screw;

a bracket connected with said body forming a lateral restraint;

a bridge extending over and connected with said body, said bridge defining an at least partially threaded bore, said bridge forming a spinal rod receiving slot between itself and said bracket; and a non-rotative wedge juxtaposing said pedicle screw and a rod received in said spinal rod receiving slot, said wedge being moveable downward by a set screw threadably mounted with in said bore in said bridge wherein said set screw is rotatable relative to said wedge with said wedge positioned underneath said set screw and with a lower portion of said set screw engaging said wedge to move said wedge downward, said wedge imparting a downward locking force on said pedicle screw head and a lateral locking force on a spinal rod against said bracket; and wherein said wedge is trapezoidal shaped in cross section and includes a first outer contact surface and a second outer contact surface opposite said first outer contact surface, said wedge positioned laterally between said generally spherical head of said pedicle screw and said spinal rod with said first outer contact surface engaged in contact with said spinal rod and said second outer contact surface engaged in contact with said generally spherical head of said pedicle screw.

* * * * *